United States Patent
Maeda et al.

(10) Patent No.: US 7,470,499 B2
(45) Date of Patent: Dec. 30, 2008

(54) ALICYCLIC UNSATURATED COMPOUND, POLYMER, CHEMICALLY AMPLIFIED RESIST COMPOSITION AND METHOD FOR FORMING PATTERN USING SAID COMPOSITION

(75) Inventors: Katsumi Maeda, Tokyo (JP); Kaichiro Nakano, Tokyo (JP)

(73) Assignee: NEC Corporation, Tokyo (JP)

( * ) Notice: Subject to any disclaimer, the term of this patent is extended or adjusted under 35 U.S.C. 154(b) by 360 days.

(21) Appl. No.: 10/548,067

(22) PCT Filed: Mar. 4, 2004

(86) PCT No.: PCT/JP2004/002728

§ 371 (c)(1),
(2), (4) Date: Sep. 6, 2005

(87) PCT Pub. No.: WO2004/078688

PCT Pub. Date: Sep. 16, 2004

(65) Prior Publication Data

US 2006/0073408 A1 Apr. 6, 2006

(30) Foreign Application Priority Data

Mar. 6, 2003 (JP) ............................... 2003-059804

(51) Int. Cl.
*G03F 7/039* (2006.01)
*G08F 32/08* (2006.01)
*C07C 35/52* (2006.01)
*C07C 69/65* (2006.01)
*C07C 43/178* (2006.01)

(52) U.S. Cl. .................. 430/270.1; 430/325; 430/326; 430/907; 526/242; 526/247; 526/268; 526/281; 526/332; 526/333; 568/665; 568/667; 568/669; 568/817; 568/579; 570/130; 570/142

(58) Field of Classification Search .................. None
See application file for complete search history.

(56) References Cited

U.S. PATENT DOCUMENTS

| | | | |
|---|---|---|---|
| 5,665,518 A | 9/1997 | Maeda et al. ............ | 430/270.1 |
| 6,673,523 B2 | 1/2004 | Kishimura et al. .......... | 430/322 |
| 6,746,722 B2 | 6/2004 | Maeda et al. ............... | 427/510 |
| 7,264,914 B2 * | 9/2007 | Feiring et al. ............ | 430/270.1 |
| 2002/0009668 A1 | 1/2002 | Nishimura et al. ........ | 430/270.1 |

FOREIGN PATENT DOCUMENTS

| | | |
|---|---|---|
| JP | 2002-338690 | 11/2002 |
| WO | WO 02/079287 A1 | 10/2002 |

OTHER PUBLICATIONS

R.R. Kunz, et al., "Outlook for 157 nm resist design", J. Vac.Sci. Technology, B17(6), Nov./Dec. 1999, 1999 American Vacuum Society, pp. 3267-3272.

Takashi Chiba, et al., "157nm Resist Materials: A Progress Report", Journal of Photopolymer Science and Technology, vol. 13, No. 4(2000), pp. 657-664.

Joice P. Mathew, et al., "(n3-Allyl)palladium(II) and Palladium(II) Nitrile Catalysts for the Addition Polymerization of Norbornene Derivatives with Functional Groups", Macromolecules 1996, vol. 29, No. 8, pp. 2755-2763.

Notification Concerning Transmittal of Copy of International Preliminary Report on Patentability (Chapter 1 of the Patent Cooperation Treaty) Form PCT/IB/326 dated Sep. 22, 2005.

* cited by examiner

*Primary Examiner*—Sin J. Lee
(74) *Attorney, Agent, or Firm*—McGinn IP Law Group, PLLC

(57) ABSTRACT

A noble alicyclic unsaturated compound represented by the general formula (1): wherein at least one of $R^1$ and $R^2$ is a fluorine atom or a fluorinated alkyl group; a polymer formed by the polymerization of a polymer precursor comprising the alicyclic compound. The polymer is useful, in the lithography using a light having a wavelength of 190 nm or less, as a chemically amplified resist which exhibits excellent transparency with respect to the light for use in exposure and also is excellent in the adhesion to a substrate and the resistance to dry etching.

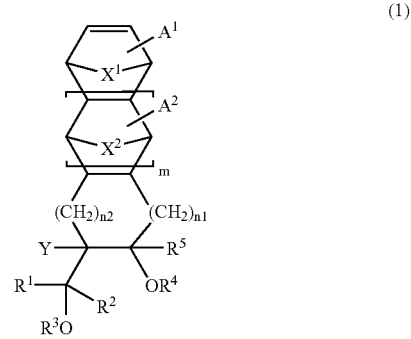

(1)

20 Claims, 1 Drawing Sheet

Transmittancy Curve of Thin Film of Polymer PA
(Thickness: 0.1μm)

US 7,470,499 B2

ALICYCLIC UNSATURATED COMPOUND, POLYMER, CHEMICALLY AMPLIFIED RESIST COMPOSITION AND METHOD FOR FORMING PATTERN USING SAID COMPOSITION

TECHNICAL FIELD

The present invention relates to a novel alicyclic unsaturated compound and a polymer of the same. In particular, the present invention relates to a polymer suitably for use in a chemically amplified resist with far ultraviolet light at a wavelength of 190 nm or less as exposure light, and to a chemically amplified resist composition using the polymer and a method for forming a pattern using the resist composition.

BACKGROUND ART

In the field of production of various electronic devices represented by semiconductor devices which must be microfabricated in the order of quarter microns, devices with higher density and integration are increasingly demanded to be produced. Accordingly, photolithographic technologies for forming a micropattern are facing more and more severe demands.

Particularly, in production of DRAMs having an integration degree of 1 G bits or more which requires a processing technology in the order of 0.13 micrometers or less, photolithography with an ArF excimer laser (193 nm) is anticipated to be used.

Recently, use of photolithography with an $F_2$ excimer laser (157 nm) has been examined for forming a more minute pattern (see R. R. Kunz et al., Journal of Vacuum Science and Technology, Vol. B17 (No. 6), pp. 3267-3272 (1999)).

Thus, a resist material applicable to photolithography using $F_2$ excimer laser light has been desired to be developed. Development of the resist for $F_2$ exposure must improve cost performance of the laser, since a gas as a material for the laser has a short life, laser equipment itself is expensive, etc. Specifically, the resist is highly demanded to have high sensitivity, in addition to high resolution corresponding to a reduction in the processing size.

A chemically amplified resist is known well, in which a photoacid generator as a sensitizer is used as means for providing the resist with high sensitivity. This resist is now widely used as a resist for a KrF excimer laser (248 nm) and a resist for an ArF excimer laser. A feature of the chemically amplified resist is that proton acid, generated by irradiation with light from a photoacid generator as a component contained in the resist, causes an acid catalyst reaction with the resist resin or the like by heating treatment after exposure. In this manner, the resist has sensitivity remarkably higher than a conventional resist with a photoreaction efficiency (reaction per photon) of less than 1. Now, most of the resists developed are chemically amplified resists.

However, in the case of photolithography using light at a short wavelength of 190 nm or less typified by $F_2$ excimer laser light, a resist for forming a micropattern is required to have a new characteristic that cannot be accomplished by a conventional material, specifically, high transparency to exposure light at 190 nm or less.

A conventional photoresist material for a KrF excimer laser or ArF excimer laser mainly employs poly(p-vinylphenol), an alicyclic resin or the like as a resin component. However, such a resin extremely highly absorbs light at a wavelength of 190 nm or less. Thus, since most of the exposure light is absorbed on the surface of the resist and is not transmitted to the substrate, a fine resist pattern cannot be formed. This is why such a conventional resin cannot be applied to photolithography using light at a short wavelength of 190 nm or less as is.

As a polymer compound transparent to $F_2$ excimer laser light (157 nm), a resin containing a fluorine atom is assumed to be promising (see R. R. Kunz et al., Journal of Vacuum Science and Technology, Vol. B17 (No. 6), pp. 3267-3272 (1999) and T. Chiba et al., Journal of Photopolymer Science and Technology, Vol. 13 (No. 4), pp. 657-664 (2000)).

DISCLOSURE OF THE INVENTION

However, a conventional fluorine-containing resin does not have sufficient transparency, adhesion to a substrate, dry etching resistance and resolution required for a resist, and cannot be used as a resin for a chemically amplified resist as is.

Therefore, a novel resin material for a resist which is highly transparent to exposure light at 190 nm or less, has excellent adhesion to a substrate and dry etching resistance, and exhibits excellent resolution has been desired.

As a result of studies to achieve the above object, the present inventors have found that a polymer obtained by polymerizing a polymer precursor containing, as a monomer, an unsaturated compound having a specific alicyclic structure as a novel compound is excellent as a chemically amplified resist. This finding has led to the completion of the present invention.

Specifically, the present invention relates to an alicyclic unsaturated compound represented by the following general formula (1):

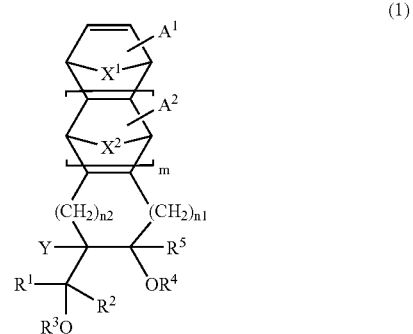

wherein $R^1$ and $R^2$ independently represent a hydrogen atom, a fluorine atom, a linear, branched or cyclic alkyl group having 1 to 6 carbon atoms or a fluorinated alkyl group, and at least one of $R^1$ and $R^2$ is a fluorine atom or a fluorinated alkyl group, $R^3$ represents a hydrogen atom, a linear, branched or cyclic alkyl group having 1 to 6 carbon atoms, a fluorinated alkyl group, a carboxymethyl group or a group that is decomposed by the action of an acid, $R^4$ represents a hydrogen atom, a linear, branched or cyclic alkyl group having 1 to 6 carbon atoms, a fluorinated alkyl group, an acetyl group, a chloroacetyl group or a group that is decomposed by the action of an acid, $R^5$ represents a hydrogen atom, a linear, branched or cyclic alkyl group having 1 to 6 carbon atoms or a fluorinated alkyl group, $A^1$ and $A^2$ independently represent a hydrogen atom or a methyl group, $X^1$ and $X^2$ independently represent —$CH_2$—, —$CH_2CH_2$— or —O—, Y represents a hydrogen atom, a methyl group or a fluorine atom, m is 0 or 1, and n1 and n2 are independently an integer of 0 to 2.

The present invention provides a polymer obtained by polymerizing a polymer precursor containing at least one compound represented by the general formula (1), specifically, a polymer having a repeating structural unit represented by the following general formula (2):

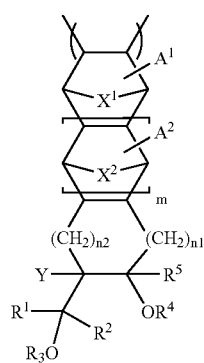

(2)

wherein $R^1$ and $R^2$ independently represent a hydrogen atom, a fluorine atom, a linear, branched or cyclic alkyl group having 1 to 6 carbon atoms or a fluorinated alkyl group, and at least one of $R^1$ and $R^2$ is a fluorine atom or a fluorinated alkyl group, $R^3$ represents a hydrogen atom, a linear, branched or cyclic alkyl group having 1 to 6 carbon atoms, a fluorinated alkyl group, a carboxymethyl group or a group that is decomposed by the action of an acid, $R^4$ represents a hydrogen atom, a linear, branched or cyclic alkyl group having 1 to 6 carbon atoms, a fluorinated alkyl group, an acetyl group, a chloroacetyl group or a group that is decomposed by the action of an acid, $R^5$ represents a hydrogen atom, a linear, branched or cyclic alkyl group having 1 to 6 carbon atoms or a fluorinated alkyl group, $A^1$ and $A^2$ independently represent a hydrogen atom or a methyl group, $X^1$ and $X^2$ independently represent —$CH_2$—, —$CH_2CH_2$— or —O—, Y represents a hydrogen atom, a methyl group or a fluorine atom, m is 0 or 1, and n1 and n2 are independently an integer of 0 to 2.

The polymer of the present invention has a fluorine atom, a group represented by $OR^4$, and an alicyclic structure. Thus, the polymer is highly transparent to light at 190 nm or less, has excellent adhesion to a substrate, and can exhibit excellent etching resistance when used as a resist resin. This is presumably because of the following reasons.

First, the polymer of the present invention has a fluorine atom, and is thus highly transparent to light at a wavelength of 190 nm or less.

Second, the resin of the present invention has a polar group represented by $OR^4$ (specifically, a hydroxyl group, an alkoxy group or an acetoxy group), and is thus assumed to have excellent adhesion to a substrate.

Third, the polymer of the present invention has an alicyclic structure, and thus has a high carbon density and can exhibit high dry etching resistance.

BEST MODE FOR CARRYING OUT THE INVENTION

Figure 1:
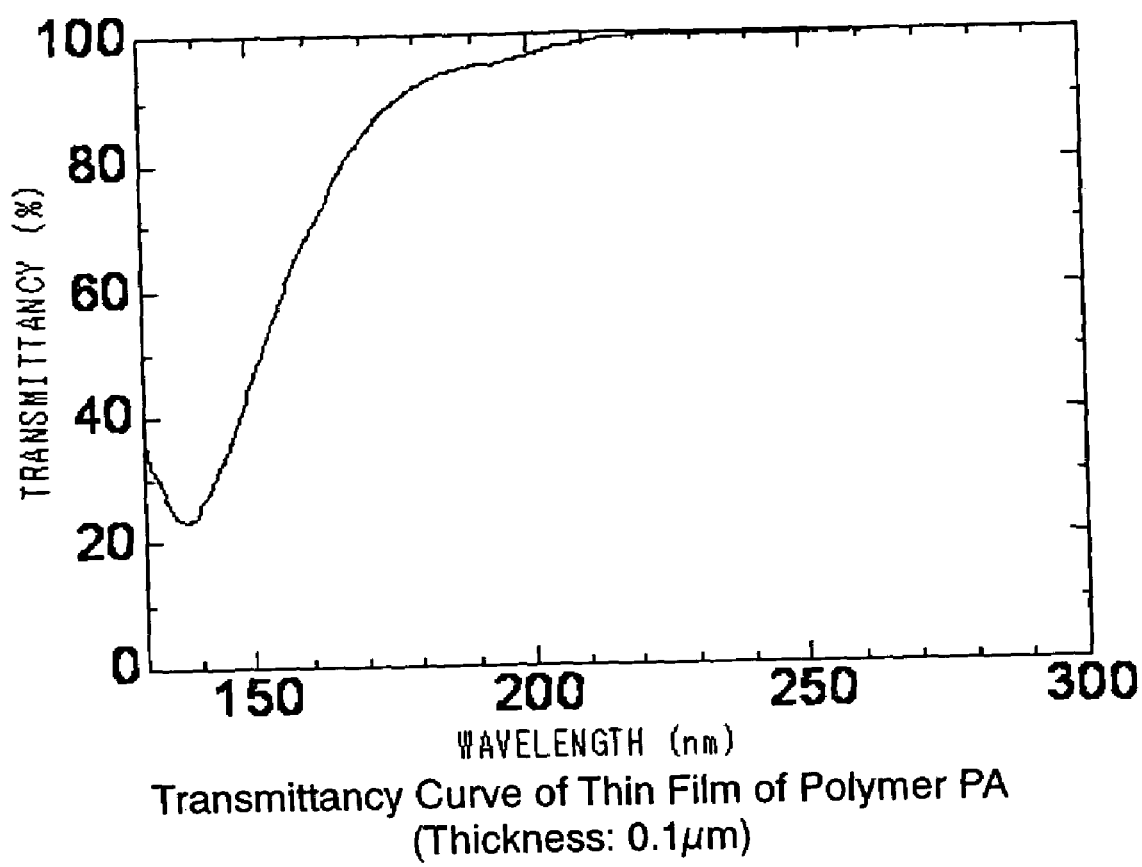
FIG. 1 is a transmittancy curve of a thin film of the polymer of the present invention (polymer PA obtained in Example 6) (thickness: 0.1 µm).

The present invention will be described in detail below.

In the general formulas (1) and (2), $R^1$ and $R^2$ independently represent a hydrogen atom, a fluorine atom, a linear, branched or cyclic alkyl group having 1 to 6 carbon atoms (of which specific examples include a methyl group, ethyl group, n-propyl group, isopropyl group, n-butyl group, isobutyl group, sec-butyl group, n-pentyl group, n-hexyl group and cyclohexyl group) or a fluorinated alkyl group (of which specific examples include a fluoromethyl group, fluoroethyl group, fluoropropyl group, difluoromethyl group, trifluoromethyl group, tetrafluoroethyl group, pentafluoroethyl group, hexafluoroisopropyl group and nonafluorohexyl group), and at least one of $R^1$ and $R^2$ is a fluorine atom or a fluorinated alkyl group.

$R^3$ represents a hydrogen atom, a linear, branched or cyclic alkyl group having 1 to 6 carbon atoms (of which specific examples include a methyl group, ethyl group, n-propyl group, isopropyl group, n-butyl group, isobutyl group, sec-butyl group, n-pentyl group and cyclohexyl group), a fluorinated alkyl group (of which specific examples include a fluoromethyl group, fluoroethyl group, fluoropropyl group, difluoromethyl group, trifluoromethyl group, tetrafluoroethyl group, pentafluoroethyl group, hexafluoroisopropyl group and nonafluorohexyl group), a carboxymethyl group (—$CH_2COOH$) or a group that is decomposed by the action of an acid (of which specific examples include a t-butyl group, t-butoxycarbonyl group, methoxymethyl group, ethoxymethyl group, menthoxymethyl group, 1-ethoxyethyl group, tetrahydropyranyl group, tetrahydrofuranyl group and a group represented by —$CH_2COOZ^1$ (wherein $Z^1$ is a group that is decomposed by the action of an acid such as a t-butyl group, tetrahydropyran-2-yl group, tetrahydrofuran-2-yl group, 4-methoxytetrahydropyran-4-yl group, 1-ethoxyethyl group, 1-butoxyethyl group, 1-propoxyethyl group, methoxymethyl group or ethoxymethyl group, or the like)).

$R^4$ represents a hydrogen atom, a linear, branched or cyclic alkyl group having 1 to 6 carbon atoms (of which specific examples include a methyl group, ethyl group, n-propyl group, isopropyl group, n-butyl group, isobutyl group, sec-butyl group, n-pentyl group and cyclohexyl group), a fluorinated alkyl group (of which specific examples include a fluoromethyl group, fluoroethyl group, fluoropropyl group, difluoromethyl group, trifluoromethyl group, tetrafluoroethyl group, pentafluoroethyl group, hexafluoroisopropyl group and nonafluorohexyl group), an acetyl group, a chloroacetyl group or a group that is decomposed by the action of an acid (of which specific examples include a t-butyl group, t-butoxycarbonyl group, methoxymethyl group, ethoxymethyl group, 1-ethoxyethyl group, tetrahydropyranyl group, tetrahydrofuranyl group and a group represented by —$CH_2COOZ^2$ (wherein $Z^2$ is a group that is decomposed by the action of an acid such as a t-butyl group, tetrahydropyran-2-yl group, tetrahydrofuran-2-yl group, 4-methoxytetrahydropyran-4-yl group, 1-ethoxyethyl group, 1-butoxyethyl group, 1-propoxyethyl group, methoxymethyl group or ethoxymethyl group, or the like)).

$R^5$ represents a hydrogen atom, a linear, branched or cyclic alkyl group having 1 to 6 carbon atoms (of which specific examples include a methyl group, ethyl group, n-propyl group, isopropyl group, n-butyl group, isobutyl group, sec-butyl group, n-pentyl group and cyclohexyl group) or a fluorinated alkyl group (of which specific examples include a fluoromethyl group, fluoroethyl group, fluoropropyl group, difluoromethyl group, trifluoromethyl group, tetrafluoroethyl group, pentafluoroethyl group, hexafluoroisopropyl group and nonafluorohexyl group).

$A^1$ and $A^2$ independently represent a hydrogen atom or a methyl group.

$X^1$ and $X^2$ independently represent —$CH_2$—, —$CH_2CH_2$— or —O—.

Y represents a hydrogen atom, a methyl group or a fluorine atom.

Further, m is 0 or 1, and n1 and n2 are independently an integer of 0 to 2.

Specific examples of the unsaturated compound having an alicyclic structure represented by the general formula (1) include the following compounds.

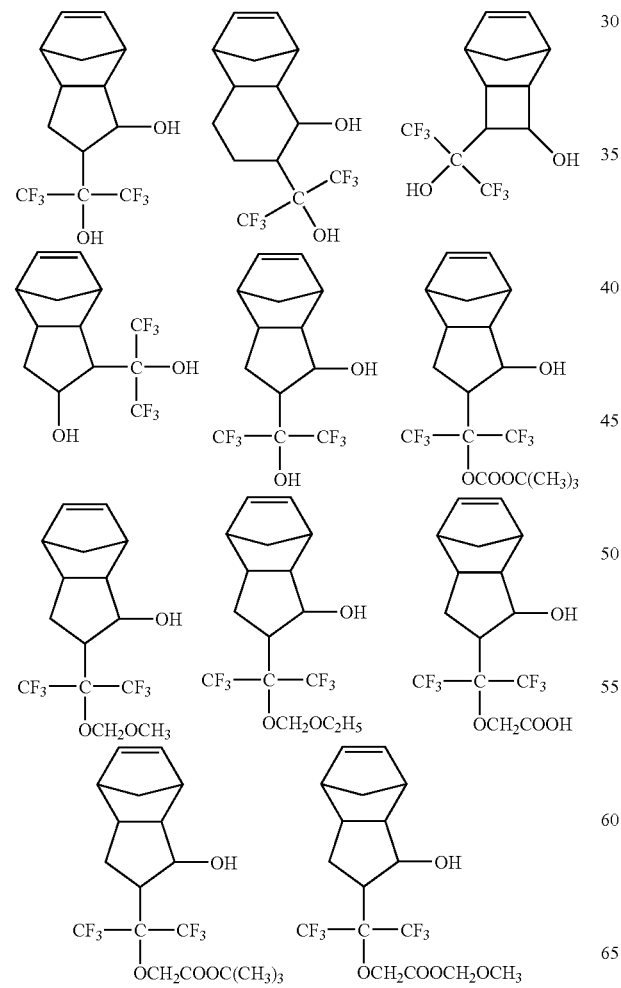

-continued

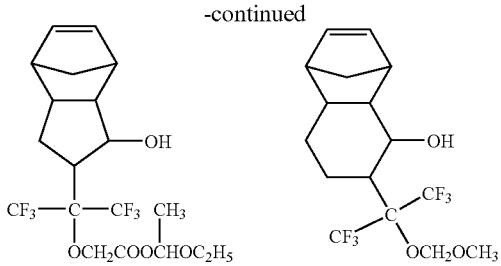

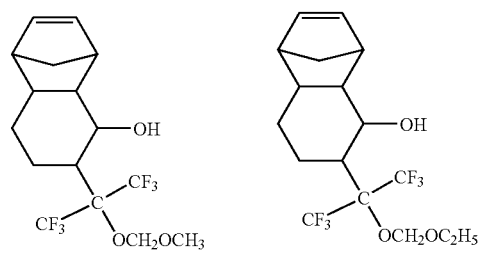

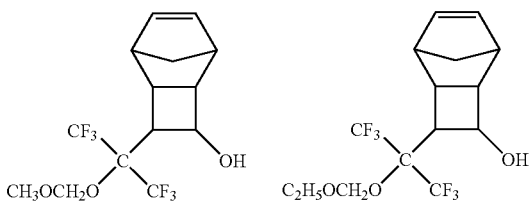

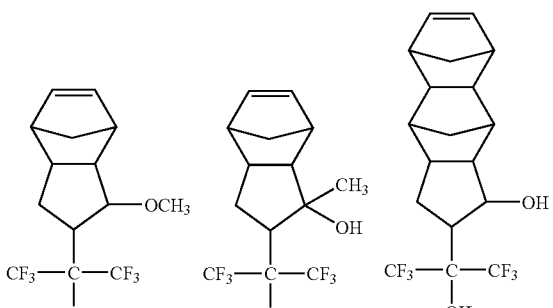

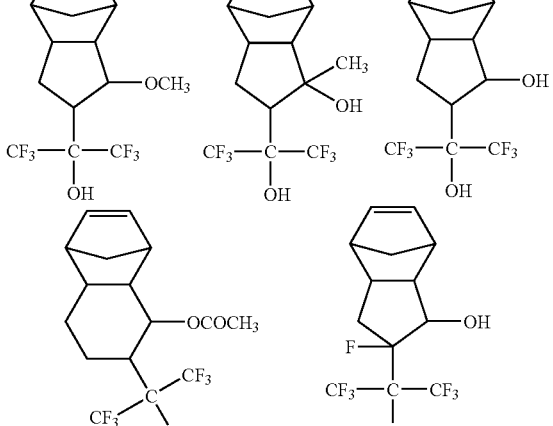

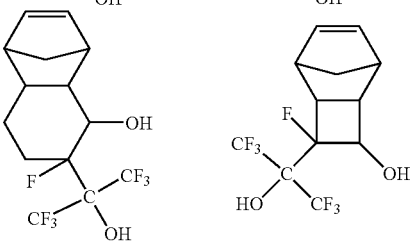

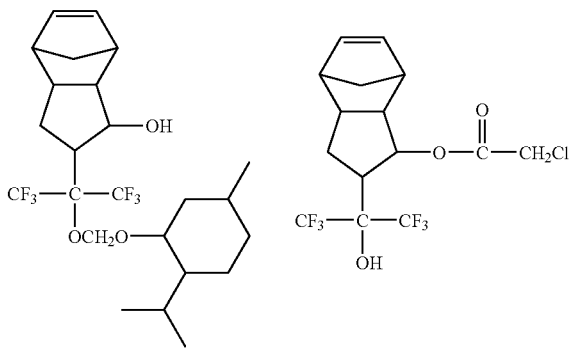

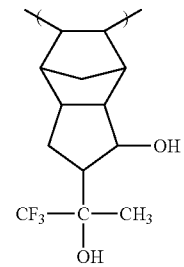

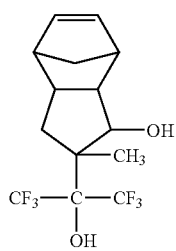

The unsaturated compound represented by the general formula (1), wherein $R^1$ and $R^2$ are a trifluoromethyl group, $R^3$, $R^4$ and $R^5$ are a hydrogen atom, $A^1$ is a hydrogen atom, $X^1$ is a methylene group (—$CH_2$—), Y is a hydrogen atom, m and n1 are 0, and n2 is 1, is synthesized as follows, for example.

First, 2-cyclopenten-1-on is reacted with dicyclopentadiene at 170 to 180° C. for 8 to 20 hours to obtain 3-oxo-tricyclo-8-decene. Then, this compound is added to a solution of lithium amide such as lithium bis(trimethylsilyl)amide in dry tetrahydrofuran under an argon atmosphere at −78° C., and then a hexafluoroacetone gas is blown into the mixture. The resulting solution is treated with an acid, and 3-oxo-4-(hexafluoro-2-hydroxyisopropyl)tricyclo[5.2.1.0$^{2,6}$]-8-decene is obtained by isolation using a conventional technique. Then, 3-oxo-4-(hexafluoro-2-hydroxyisopropyl)tricyclo[5.2.1.0$^{2,6}$]-8-decene is reduced by a reducing agent such as lithium aluminum hydride to obtain the intended unsaturated compound.

Examples of the repeating structural unit represented by the general formula (2) include the following.

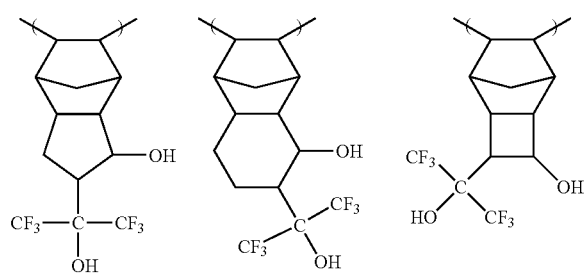

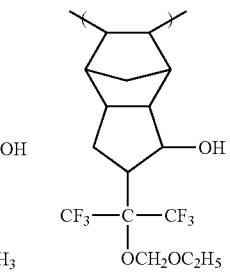

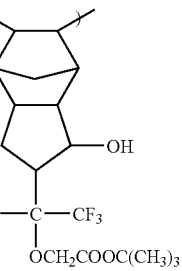

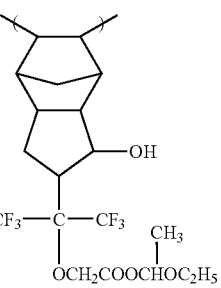

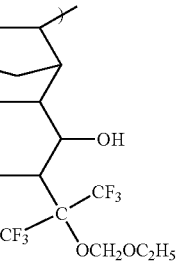

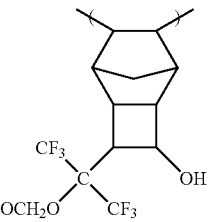

-continued

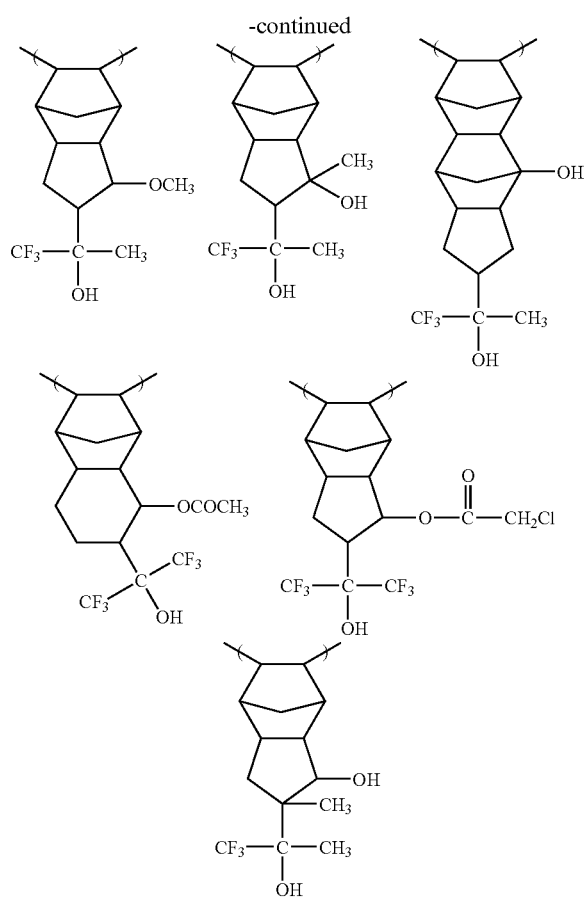

The compound represented by the general formula (1) may not only form a homopolymer, but also be copolymerized with a comonomer which can provide the resulting polymer with characteristics useful for a chemically amplified resist. Examples of the repeating structural unit derived from such a comonomer include structural units represented by the following general formulas (3) to (9), since these structural units can be sufficiently polymerized with the corresponding monomer, and at least one of the structural units is preferable.

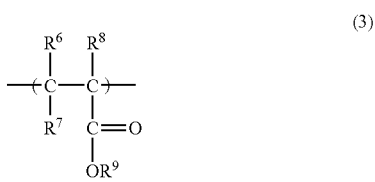

(3)

In the formula (3), $R^6$ and $R^7$ independently represent a hydrogen atom or a fluorine atom, $R^8$ is a hydrogen atom, a fluorine atom, a methyl group or a trifluoromethyl group, and $R^9$ represents a hydrogen atom, a linear, branched or cyclic alkyl group having 1 to 20 carbon atoms (of which specific examples include a methyl group, ethyl group, n-propyl group, isopropyl group, n-butyl group, isobutyl group, sec-butyl group, n-pentyl group, cyclohexyl group, norbornyl group, isobornyl group, adamantyl group and tricyclodecyl group), a fluorinated alkyl group (of which specific examples include a fluoromethyl group, fluoroethyl group, fluoropropyl group, difluoromethyl group, trifluoromethyl group, tetrafluoroethyl group, pentafluoroethyl group, hexafluoroisopropyl group and nonafluorohexyl group), a group that is decomposed by the action of an acid (of which specific examples include a t-butyl group, tetrahydropyran-2-yl group, tetrahydrofuran-2-yl group, 4-methoxytetrahydropyran-4-yl group, 1-ethoxyethyl group, 1-butoxyethyl group, 1-propoxyethyl group, 3-oxocyclohexyl group, 2-methyl-2-adamantyl group, 2-ethyl-2-adamantyl group, 1-methyl-1-adamantylethyl group, 8-methyl-8-tricyclo[5.2.1.0$^{2,6}$]decyl group, 1,2,7,7-tetramethyl-2-norbornyl group, 2-acetoxymenthyl group, 2-hydroxymenthyl group, 1-methyl-1-cyclohexylethyl group, methoxymethyl group and ethoxymethyl group), an alicyclic hydrocarbon group having 7 to 13 carbon atoms which has a group that is decomposed by the action of an acid (of which specific examples include alicyclic hydrocarbon groups having 7 to 13 carbon atoms which have a group that is decomposed by the action of an acid as described in Japanese Patent No. 2856116) or a 2,6-norbornanecarbolactone-5-yl group.

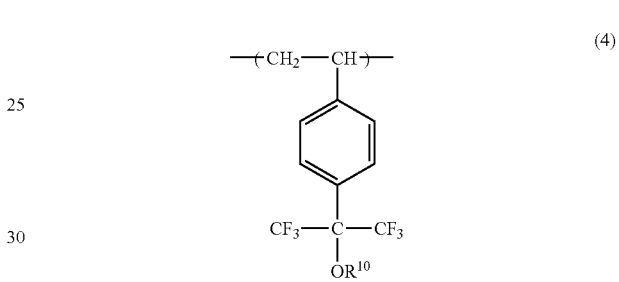

(4)

In the formula (4), $R^{10}$ represents a hydrogen atom or a group that is decomposed by the action of an acid (of which specific examples include a t-butyl group, t-butoxycarbonyl group, methoxymethyl group, ethoxymethyl group, 1-ethoxyethyl group, tetrahydropyranyl group, tetrahydrofuranyl group and a group represented by —CH$_2$COOZ$^3$ (wherein Z$^3$ is a t-butyl group, tetrahydropyran-2-yl group, tetrahydrofuran-2-yl group, 4-methoxytetrahydropyran-4-yl group, 1-ethoxyethyl group, 1-butoxyethyl group, 1-propoxyethyl group, methoxymethyl group, ethoxymethyl group or the like)).

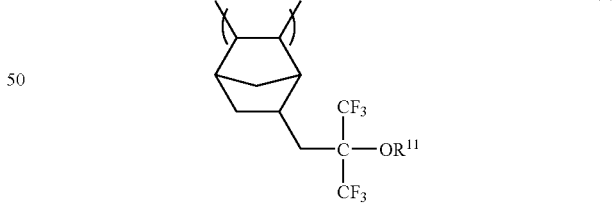

(5)

In the formula (5), $R^{11}$ represents a hydrogen atom or a group that is decomposed by the action of an acid (of which specific examples include a t-butyl group, t-butoxycarbonyl group, methoxymethyl group, ethoxymethyl group, 1-ethoxyethyl group, tetrahydropyranyl group, tetrahydrofuranyl group and a group represented by —CH$_2$COOZ$^4$ (wherein Z$^4$ is a t-butyl group, tetrahydropyran-2-yl group, tetrahydrofuran-2-yl group, 4-methoxytetrahydropyran-4-yl group, 1-ethoxyethyl group, 1-butoxyethyl group, 1-propoxyethyl group, methoxymethyl group, ethoxymethyl group, or the like)).

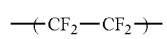 (6)

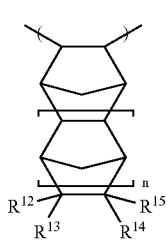 (7)

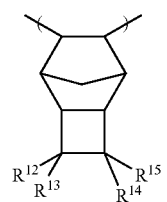 (8)

In the formulas (7) and (8), $R^{12}$, $R^{13}$, $R^{14}$ and $R^{15}$ independently represent a hydrogen atom, a fluorine atom, a methyl group, a trifluoromethyl group, a hydroxy group, a hydroxyalkyl group (of which specific examples include a hydroxymethyl group and hydroxyethyl group), a carboxy group (—COOH), —CH$_2$OC(CF$_3$)$_2$CH$_2$COOZ$^5$ (wherein $Z^5$ is a hydrogen atom or a group that is decomposed by the action of an acid (of which specific examples include a t-butyl group, tetrahydropyran-2-yl group, tetrahydrofuran-2-yl group, 4-methoxytetrahydropyran-4-yl group, 1-ethoxyethyl group, 1-butoxyethyl group, 1-propoxyethyl group, 3-oxocyclohexyl group, 2-methyl-2-adamantyl group, 2-ethyl-2-adamantyl group, 1-methyl-1-adamantylethyl group, 8-methyl-8-tricyclo[5.2.1.0$^{2,6}$]decyl group, 1,2,7,7-tetramethyl-2-norbornyl group, 2-acetoxymenthyl group, 2-hydroxymenthyl group, 1-methyl-1-cyclohexylethyl group, methoxymethyl group and ethoxymethyl group)) or an acid-dissociable organic group having 20 or less carbon atoms which is decomposed by the action of an acid to produce a carboxy group (of which specific examples include a t-butoxycarbonyl group, tetrahydropyranyloxycarbonyl group, tetrahydrofuranyloxycarbonyl group, 4-methoxytetrahydropyranyloxycarbonyl group, 1-ethoxyethoxycarbonyl group, 1-butoxyethoxycarbonyl group, 1-propoxyethoxycarbonyl group, 3-oxocyclohexyloxycarbonyl group, 2-methyl-2-adamantyloxycarbonyl group, 2-ethyl-2-adamantyloxycarbonyl group, 8-methyl-8-tricyclo[5.2.1.0$^{2,6}$]decyloxycarbonyl group, 1,2,7,7-tetramethyl-2-norbornyloxycarbonyl group, 2-acetoxymenthyloxycarbonyl group, 2-hydroxymenthyloxycarbonyl group, 1-methyl-1-cyclohexylethoxycarbonyl group, methoxymethoxycarbonyl group and ethoxymethoxycarbonyl group). In the formula (7), n is 0 or 1.

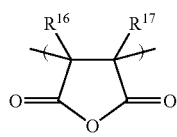 (9)

In the formula (9), $R^{16}$ and $R^{17}$ independently represent a hydrogen atom, a fluorine atom or a trifluoromethyl group.

From the viewpoint of performance of the resulting polymer, the repeating structural unit represented by the general formula (2) is contained in the polymer preferably at 5 to 100 mol %, and more preferably at 10 to 100 mol %.

The above polymer can be obtained by a common polymerization method such as radical polymerization, anionic polymerization or addition polymerization.

In the case of radical polymerization, the polymer is produced by adding a suitable radical polymerization initiator (such as 2,2'-azobis(isobutylonitrile)) to the monomer(s) in dry tetrahydrofuran under an atmosphere of an inert gas (such as argon or nitrogen), and heating and stirring the mixture at 50 to 70° C. for 0.5 to 24 hours.

In the case of addition polymerization, the polymer can be produced using a palladium compound (such as {(η$^3$-allyl)Pd(BF$_4$)}, {(η$^3$-allyl)Pd(SbF$_6$)} or [Pd(CH$_3$CN)$_4$][BF$_4$]$_2$) as a catalyst, according to the method of J. P. Mathew et al. (see Macromolecules, Vol. 29, pp. 2755-2763 (1996)), or using a nickel compound [bis(pentafluorophenyl)nickel-toluene complex] or the like as a catalyst, according to the method of T. Chiba et al. (see Journal of Photopolymer Science and Technology, Vol. 13 (No. 4), 657-664 (2000)).

The polymer has a weight average molecular weight of preferably 2,000 to 200,000, and more preferably 4,000 to 100,000.

The polymer as described above is mixed with at least a photoacid generator which generates an acid upon exposure to prepare the chemically amplified resist composition of the present invention.

The photoacid generator used for the chemically amplified resist composition is preferably a photoacid generator which generates an acid by irradiation with light at 130 to 190 nm, and is not specifically limited insofar a mixture of the photoacid generator with the polymer of the present invention and other components can be sufficiently dissolved in an organic solvent, and a homogeneous coating film can be formed using the solution by a film-forming method such as spin coating. The photoacid generator may be used singly or in a mixture of two or more.

Examples of the photoacid generator that can be used include, but are not limited to, a triarylsulfonium salt derivative, a diaryliodonium salt derivative, a dialkylphenacylsulfonium salt derivative, a nitrobenzylsulfonate derivative and a sulfonic acid ester derivative of N-hydroxysuccinimide.

In order to provide the chemically amplified resist composition with sufficient sensitivity and allow formation of a good pattern, the content of the photoacid generator is preferably 0.2% or more by weight, and more preferably 1% or more by weight based on the polymer and the photoacid generator in total. On the other hand, in order to form a homogeneous coating film and suppress production of a residue (scum) after development, the content is preferably 30% or less by weight, and more preferably 15% or less by weight.

A suitable solvent is used, if necessary, when the chemically amplified resist composition is prepared.

The solvent used herein is not specifically limited, insofar as the solvent is an organic solvent which can sufficiently dissolve components consisting of the polymer and the photoacid generator therein to provide a solution that can form a homogeneous coating film by a method such as spin coating. The solvent may be used singly or in a mixture of two or more.

Specific examples of the solvent include, but are obviously not limited to, n-propyl alcohol, isopropyl alcohol, n-butyl alcohol, t-butyl alcohol, propylene glycol monomethyl ether acetate, propylene glycol monoethyl ether acetate, ethyl lactate, 2-methoxybutyl acetate, 2-ethoxyethyl acetate, methyl pyruvate, ethyl pyruvate, methyl 3-methoxypropionate, ethyl 3-methoxypropionate, N-methyl-2-pyrrolidinone, cyclohexanone, cyclopentanone, cyclohexanol, methyl ethyl ketone, 1,4-dioxane, ethylene glycol monomethyl ether, ethylene glycol monomethyl ether acetate, ethylene glycol monoethyl ether, ethylene glycol monoisopropyl ether, diethylene glycol monomethyl ether and diethylene glycol dimethyl ether.

Further, the chemically amplified resist can be prepared by adding, if necessary, other components such as a dissolution inhibitor, an organic base, a surfactant, a pigment, a stabilizer, a coating properties improver and a dye, in addition to the polymer, the photoacid generator and the solvent.

The chemically amplified resist obtained as above is applied to a substrate to be processed, exposed to light at a wavelength of 130 to 190 nm, heated if necessary, and then developed, so that a pattern can be formed.

The exposure light is preferably $F_2$ excimer laser light.

EXAMPLES

The present invention will now be described in more detail by way of examples. These examples should not be construed as limiting the present invention.

Example 1

Synthesis of a compound A of the general formula (1), wherein $R^1$ and $R^2$ are a trifluoromethyl group, $R^3$ to $R^5$ are a hydrogen atom, $A^1$ is a hydrogen atom, $X^1$ is a methylene group, Y is a hydrogen atom, m and n1 are 0, and n2 is 1 (3-hydroxy-4-(hexafluoro-2-hydroxyisopropyl)tricyclo [$5.2.1.0^{2,6}$]-8-decene, see the following structural formula (A))

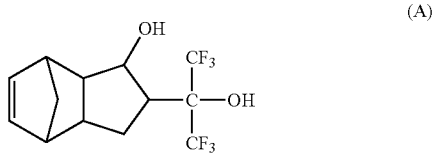

24.5 g of 2-cyclopenten-1-one and 79 g of dicyclopentadiene were stirred at 175° C. for 15 hours. The mixture was left to be cooled, and then distilled under reduced pressure (70 to 71° C./0.8 mmHg) to obtain 7 g of 3-oxotricyclo[$5.2.1.0^{2,6}$]- 8-decene.

A solution of 12 g of the resulting 3-oxotricyclo [$5.2.1.0^{2,6}$]-8-decene in 15 ml of dry tetrahydrofuran (hereinafter abbreviated to THF) was added dropwise to 100 ml of a 1 mol/L solution of lithium bis(trimethylsilyl)amide in THF under an argon atmosphere at −78° C. After one hour, a hexafluoroacetone gas (generated from 53.5 g of hexafluoroacetone hydrate and 100 ml of sulfuric acid) was blown into the mixture, which was further stirred for 30 minutes. Next, 0.5 N hydrochloric acid was added to the reaction solution to make the solution acidic, and the organic layer was extracted with 200 ml of diethyl ether. The resulting organic layer was washed with brine and then dried over magnesium sulfate, and the solvent was removed by an evaporator. The residue was distilled under reduced pressure (79 to 80° C./0.3 mmHg) to obtain 16.54 g of 3-oxo-4-(hexafluoro-2-hydroxyisopropyl)tricyclo[$5.2.1.0^{2,6}$]-8-decene.

0.679 g of lithium aluminum hydride was dispersed in 20 ml of dry diethyl ether. A solution of 3 g of the resulting 3-oxo-4-(hexafluoro-2-hydroxyisopropyl)tricyclo [$5.2.1.0^{2,6}$]-8-decene in 10 ml of dry diethyl ether was added dropwise to the dispersion under an argon atmosphere. After stirring at room temperature for five hours, water was added to the mixture under cooling with ice to decompose the unreacted lithium aluminum hydride, and 10% sulfuric acid was further added to make the solution acidic. The organic layer was extracted with 200 ml of diethyl ether, washed with brine, a 3% aqueous solution of sodium hydrogencarbonate and brine in this order, and then dried over magnesium sulfate. Next, the solvent was evaporated under reduced pressure. The residue was crystallized from hexane to obtain 1.33 g of the intended compound A (white solid, yield: 44%).

Analytical data:
$^1$H-NMR ($\delta$ (CDCl$_3$)): 1.2-1.8 (4H, m), 1.9-2.45 (2H, m), 2,6-3.0 (4H, m), 4.6-4.75 (1H, m), 5.52 and 5.53 (0.6H in total, s) and 6.1-6.5 (2.4H, m). IR (KBr): 3481 and 3233 ($\nu_{O-H}$), 2974 and 2948 ($\nu_{C-H}$), 1300, 1276, 1237, 1204, 1147 and 1130 cm$^{-1}$.

Example 2

Synthesis of a compound B of the general formula (1), wherein $R^1$ and $R^2$ are a trifluoromethyl group, $R^3$ to $R^5$ are a hydrogen atom, $A^1$ is a hydrogen atom, $X^1$ is a methylene group, Y is a hydrogen atom, m and n1 are 0, and n2 is 2 (3-hydroxy-4-(hexafluoro-2-hydroxyisopropyl)tricycle [$6.2.1.0^{2,7}$]-9-undecene, see the following structural formula (B))

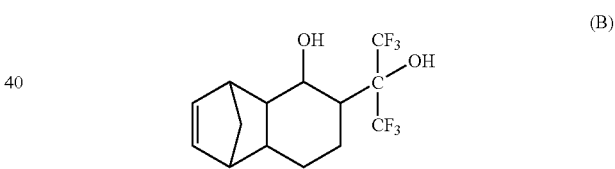

The intended compound B was produced in the same manner as Example 1, except for using 2-cyclohexen-1-on in place of 2-cyclopenten-1-on in Example 1 (total yield: 10%).

Analytical data:
$^1$H-NMR ($\delta$ (CDCl$_3$)): 1.0-2.0 (7H, m), 2.4 and 2.41 (1H in total, s), 2.55-3.2 (4H, m), 4.58-4.56 (1H, m), 6.85 and 7.0 (1H in total, s) and 6.1-6.35 (2H, m). IR (KBr): 3481 and 3233 ($\nu_{O-H}$), 2975 and 2947 ($\nu_{C-H}$), 1299, 1275, 1233, 1200, 1143 and 1127 cm$^{-1}$.

Example 3

Synthesis of a compound C of the general formula (1), wherein $R^1$ and $R^2$ are a trifluoromethyl group, $R^3$ is a hydrogen atom, $R^4$ is a chloroacetyl group, $R^5$ is a hydrogen atom, $A^1$ is a hydrogen atom, $X^1$ is a methylene group, Y is a hydrogen atom, m and n1 are 0, and n2 is 1 (3-chloroacetyl-4-(2-hydroxyhexafluoroisopropyl)tricyclo[$5.2.1.0^{2,6}$]-8-decene, see the following structural formula (C))

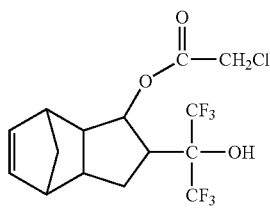
(C)

3 g of the compound A obtained in Example 1 and 2.25 g of pyridine were dissolved in 30 ml of dry THF, and then 2.18 g of chloroacetic anhydride was added to the solution under cooling with ice, and the mixture was stirred for seven hours. The solution was poured into ice water, and the organic layer was extracted with 100 ml of diethyl ether, and washed with 0.5 N hydrochloric acid, brine, a 1% aqueous solution of sodium hydrogencarbonate and brine in this order. The organic layer was dried over magnesium sulfate, and the solvent was evaporated under reduced pressure to obtain 3.67 g of the intended compound C (white solid, yield: 99%).

Analytical data:
$^1$H-NMR (δ (CDCl$_3$)): 1.3-2.4 (5H, m), 2.5-3.1 (4H, m), 3.4 and 4.2-4.4 (1H in total, m), 4.05-4.2 (2H, m), 5.3-5.65 (1H, m) and 5.95-6.3 (2H, m).

Example 4

Synthesis of a compound D of the general formula (1), wherein R$^1$ and R$^2$ are a trifluoromethyl group, R$^3$ is an ethoxymethyl group, R$^4$ and R$^5$ are a hydrogen atom, A$^1$ is a hydrogen atom, X$^1$ is a methylene group, Y is a hydrogen atom, m and n1 are 0, and n2 is 1 (3-hydroxy-4-(2-ethoxymethoxyhexafluoroisopropyl)tricyclo[5.2.1.0$^{2,6}$]-8-decene, see the following structural formula (D))

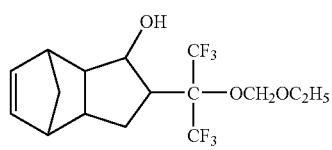
(D)

19.14 g of the compound C obtained in Example 3 and 23.47 g of N,N-diisopropylethylamine were dissolved in 150 ml of dry methylene chloride. 13.74 g of chloromethyl ethyl ether was added to the solution, and the mixture was stirred at room temperature for five days. The mixture was concentrated under reduced pressure, 200 ml of diethyl ether was added to the residue, and the organic layer was washed with 0.1 N hydrochloric acid, brine, a 1% aqueous solution of sodium hydrogen carbonate and brine in this order. The organic layer was dried over magnesium sulfate, and the solvent was evaporated under reduced pressure to obtain 20.78 g of a compound with a hexafluoroisopropanol group ethoxymethylated (viscous liquid, yield: 92%). Next, 9.7 g of the ethoxymethylated compound was dissolved in 200 ml of 90% methanol, 5.374 g of potassium carbonate was added to the solution, and the mixture was stirred at room temperature. After three hours, the mixture was concentrated under reduced pressure, 100 ml of diethyl ether was added to the residue, and the organic layer was washed with brine. The organic layer was dried over magnesium sulfate, and the solvent was evaporated under reduced pressure to obtain 7.28 g of the intended compound D (viscous liquid, yield: 94%).

Analytical data:
$^1$H-NMR (δ (CDCl$_3$)): 1.19-1.3 (3H, m), 1.35-2.25 (5H, m), 2.39-2.42 (1H, m), 2.58-3.05 (4H, m), 3.6-3.8 (2H, m), 4.45-4.6 (1H, m), 5.0-5.1 (2H, m), 6.08-6.34 (2H, m). IR (KBr): 3487 (ν$_{O-H}$), 2981 (ν$_{C-H}$), 1267, 1210, 1179, 1144, 1106 and 1054 cm$^{-1}$.

Example 5

Synthesis of a compound E of the general formula (1), wherein R$^1$ and R$^2$ are a trifluoromethyl group, R$^3$ is a menthoxymethyl group, R$^4$ and R$^5$ are a hydrogen atom, A$^1$ is a hydrogen atom, X$^1$ is a methylene group, Y is a hydrogen atom, m and n1 are 0, and n2 is 1 (3-hydroxy-4-(2-menthoxymethoxyhexafluoroisopropyl)tricyclo[5.2.1.0$^{2,6}$]-8-decene, see the following structural formula (E))

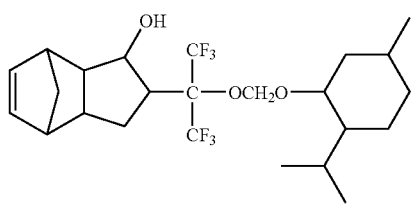
(E)

The intended compound E was synthesized in the same manner as Example 4, except for using chloromethyl menthyl ether in place of chloromethyl ethyl ether in Example 4 (total yield: 10%).

Analytical data:
$^1$H-NMR (δ (CDCl$_3$)): 0.75-1.1 (12H, m), 1.2-1.7 (7H, m), 1.75-2.25 (4H, m), 2.35-3.1 (5H, m), 3.3-3.45 (1H, m), 4.4-4.65 (1H, m), 4.9-5.25 (2H, m), 6.1-6.35 (2H, m).

Example 6

Synthesis of a polymer PA composed of 100 mol % of a structural unit F of the general formula (2), wherein R$^1$ and R$^2$ are a trifluoromethyl group, R$^3$ to R$^5$ are a hydrogen atom, A$^1$ is a hydrogen atom, X$^1$ is a methylene group, Y is a hydrogen atom, m and n1 are 0, and n2 is 1 (see the following structural formula (F))

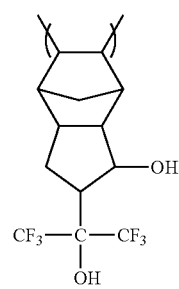
(F)

0.208 g of di-μ-chlorobis[(η$^3$-allyl)palladium (II)] and 0.391 g of silver hexafluoroantimonate were dissolved in 12 ml of methylene chloride, and the mixture was stirred at room temperature. After 30 minutes, the reaction mixture was filtered, the filtrate was added to a solution of 9 g of the compound A obtained in Example 1 in 100 ml of methylene chloride, and the mixture was stirred at room temperature for 68 hours. The deposited resin was separated by filtration, and the resin was dissolved in acetone and reprecipitated in hexane. The deposited resin was separated by filtration to obtain 3.3 g of a resin. Next, 3.3 g of the resulting resin was dissolved in 33 ml of methanol. 0.438 g of sodium borohydride was added to the solution under cooling with ice, and the mixture was allowed to stand for 30 minutes. The deposited black precipitate was separated by filtration, the filtrate was poured into a mixture of 3.3 ml of hydrochloric acid with 300 ml of water, and the deposited polymer was separated by filtration. Next, the polymer was dissolved in 100 ml of diethyl ether. The polymer solution was dried over magnesium sulfate, and then the solvent was evaporated under reduced pressure. A small amount of acetone was added to the residue, which was reprecipitated in hexane to obtain 2.59 g of a intended polymer PA (yield: 29%).

The resulting polymer PA had a weight average molecular weight (Mw) of 9,600 (as polystyrene) and a degree of dispersion (Mw/Mn) of 2.01.

Example 7

Synthesis of a polymer PB composed of 50 mol % of the structural unit F and 50 mol % of a structural unit G of the general formula (2), wherein $R^1$ and $R^2$ are a trifluoromethyl group, $R^3$ is an ethoxymethyl group, $R^4$ and $R^5$ are a hydrogen atom, $A^1$ is a hydrogen atom, $X^1$ is a methylene group, Y is a hydrogen atom, m and n1 are 0, and n2 is 1 (see the following structural formula (G))

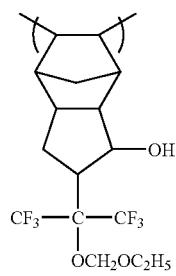

(G)

0.309 g of di-μ-chlorobis[($\eta^3$-allyl)palladium (II)] and 0.579 g of silver hexafluoroantimonate were dissolved in 15 ml of methylene chloride, and the mixture was stirred at room temperature. After 30 minutes, the reaction mixture was filtered, and the filtrate was added to a solution of 4 g of the compound A obtained in Example 1 and 11.05 g of the compound D obtained in Example 4 in 30 ml of methylene chloride. The mixture was stirred at room temperature for 15 hours, and the solution was added to 300 ml of hexane. The deposited resin was separated by filtration to obtain 7.35 g of a resin. Next, 7.35 g of the resulting resin was dissolved in 73 ml of methanol. 0.184 g of sodium borohydride was added to the solution under cooling with ice, and the mixture was allowed to stand for 30 minutes. The deposited black precipitate was separated by filtration, the filtrate was poured into 700 ml of a 5% aqueous solution of ammonium chloride, and the deposited polymer was separated by filtration. Next, the polymer was dissolved in 200 ml of diethyl ether. The polymer solution was dried over magnesium sulfate, and then the solvent was evaporated under reduced pressure. A small amount of acetone was added to the residue, which was reprecipitated in hexane to obtain 4.78 g of the intended polymer PB (yield: 32%).

The resulting polymer PB had a weight average molecular weight (Mw) of 12,300 (as polystyrene) and a degree of dispersion (Mw/Mn) of 2.12.

Example 8

Synthesis of a polymer PC composed of 50 mol % of the structural unit F and 50 mol % of a structural unit H of the general formula (2), wherein $R^1$ and $R^2$ are a trifluoromethyl group, $R^3$ is a menthoxymethyl group, $R^4$ and $R^5$ are a hydrogen atom, $A^1$ is a hydrogen atom, $X^1$ is a methylene group, Y is a hydrogen atom, m and n1 are 0, and n2 is 1 (see the following structural formula (H))

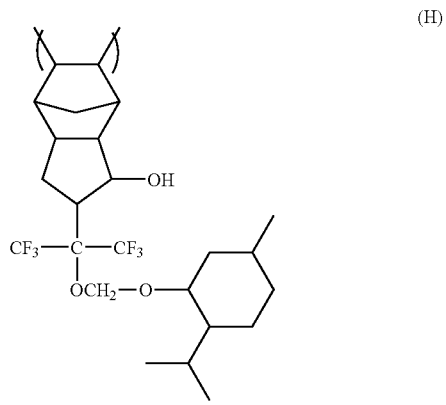

(H)

The intended polymer PC was produced in the same manner as Example 7, except for using in Example 7 the compound E obtained in Example 5 in place of the compound D obtained in Example 4 (total yield: 19%).

The resulting polymer PC had a weight average molecular weight (Mw) of 14,200 (as polystyrene) and a degree of dispersion (Mw/Mn) of 2.23.

Example 9

Synthesis of a polymer PD composed of 80 mol % of the structural unit F and 20 mol % of a structural unit I of the general formula (5), wherein $R^{11}$ is an ethoxymethyl group (see the following structural formula (I))

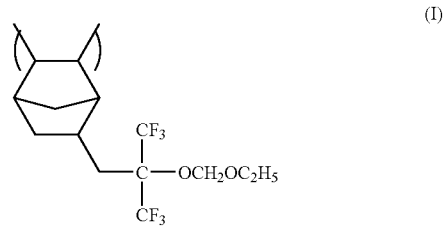

(I)

0.174 g of di-μ-chlorobis[($\eta^3$-allyl)palladium (II)] and 0.326 g of silver hexafluoroantimonate were dissolved in 10 ml of methylene chloride, and the mixture was stirred at room temperature. After 30 minutes, the reaction mixture was filtered, and the filtrate was added to a solution of 6 g of the compound A obtained in Example 1, 1.58 g of 5-(2-trifluoromethyl-3,3,3-trifluoro-2-ethoxymethoxypropyl)-2-norbornene and 0.1 g of 1,8-bis(dimethylamino)naphthalene in 40 ml of methylene chloride. The mixture was stirred at room temperature for 72 hours, the solution was added to 300 ml of hexane, and the deposited resin was separated by filtration. Then, a resin was dissolved in a small amount of acetone, the solution was poured into water, and the deposited resin was separated by filtration. Further, the resin was dissolved in a small amount of acetone and was reprecipitated in 200 ml of hexane to obtain 3.56 g of the intended polymer PD (yield: 47%).

The resulting polymer PD had a weight average molecular weight (Mw) of 10,500 (as polystyrene) and a degree of dispersion (Mw/Mn) of 2.15.

Example 10

Synthesis of a polymer PE composed of 33 mol % of the structural unit F, 37 mol % of a structural unit J of the general formula (3), wherein $R^6$ and $R^7$ are a hydrogen atom, $R^8$ is a trifluoromethyl group, and $R^9$ is a methyl group (see the following structural formula (J)), and 30 mol % of a structural unit K of the general formula (3), wherein $R^6$ and $R^7$ are a hydrogen atom, $R^8$ is a trifluoromethyl group, and $R^9$ is a t-butyl group (see the following structural formula (K))

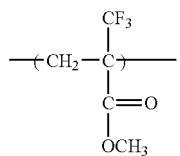

(J)

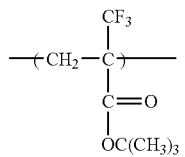

(K)

4 g of the compound A obtained in Example 1, 2.18 g of methyl 2-(trifluoromethyl)acrylate and 2.26 g of t-butyl 2-(trifluoromethyl)acrylate were dissolved in 4 ml of dry THF. 0.252 g of 2,2'-azobis(isobutylonitrile) was added to the solution, and the mixture was heated to reflux under an argon atmosphere for 20 hours. The mixture was left to be cooled and then added to 100 ml of hexane. The deposited resin was separated by filtration to obtain 2.2 g of the intended polymer PE (yield: 26%).

The resulting polymer PE had a weight average molecular weight (Mw) of 8,700 (as polystyrene) and a degree of dispersion (Mw/Mn) of 2.22.

Example 11

Synthesis of a polymer PF composed of 33 mol % of a structural unit L of the general formula (2), wherein $R^1$ and $R^2$ are a trifluoromethyl group, $R^3$ to $R^5$ are a hydrogen atom, $A^1$ is a hydrogen atom, $X^1$ is a methylene group, Y is a hydrogen atom, m and n1 are 0, and n2 is 2 (see the following structural formula (L)), 37 mol % of the structural unit J and 30 mol % of the structural unit K

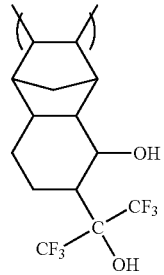

(L)

2.5 g of the intended polymer PF was obtained in the same manner as Example 10, except for using 4.18 g of the compound B obtained in Example 2 in place of the compound A in Example 10 (yield: 29%).

The resulting polymer PF had a weight average molecular weight (Mw) of 10,200 (as polystyrene) and a degree of dispersion (Mw/Mn) of 2.34.

Example 12

Synthesis of a polymer PG composed of 80 mol % of the structural formula F and 20 mol % of a structural unit M of the general formula (7), wherein $R^{12}$ to $R^{14}$ are a hydrogen atom, $R^{15}$ is —$CH_2OC(CF_3)_2CH_2COOH$ and n is 0 (see the following structural formula (M))

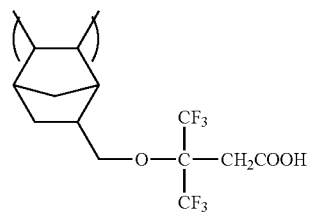

(M)

0.331 g of di-μ-chlorobis[(η³-allyl)palladium (II)] and 0.621 g of silver hexafluoroantimonate were dissolved in 20 ml of methylene chloride, and the mixture was stirred at room temperature. After 30 minutes, the reaction mixture was filtered, and the filtrate was added to a solution of 11.43 g of the compound A obtained in Example 1 and 3 g of 3-bis(trifluoromethyl)-3-(5-norbornene-2-ylmethyloxy)propionic acid in 110 ml of methylene chloride. The mixture was stirred at room temperature for 72 hours, and the deposited resin was separated by filtration to obtain 7.06 g of a resin. Next, 7.06 g of the resulting resin was dissolved in 70 ml of methanol. 0.93 g of sodium borohydride was added to the solution under cooling with ice, and the mixture was allowed to stand for 30 minutes. The deposited black precipitate was separated by filtration, the filtrate was poured into a mixture of 7 ml of concentrated hydrochloric acid with 700 ml of water, and the deposited polymer was separated by filtration. Next, the polymer was dissolved in 200 ml of ether, the organic layer was dried over magnesium sulfate, and then the solvent was evaporated under reduced pressure. A small amount of acetone was added to the residue, which was reprecipitated in hexane to obtain 4.9 g of the intended polymer PG (yield: 34%).

The resulting polymer PG had a weight average molecular weight (Mw) of 10,400 (as polystyrene) and a degree of dispersion (Mw/Mn) of 2.08.

Example 13

Synthesis of a polymer PH composed of 80 mol % of the structural formula F and 20 mol % of a structural unit N of the general formula (7), wherein $R^{12}$ to $R^{14}$ are a hydrogen atom, $R^{15}$ is —$CH_2OC(CF_3)_2CH_2COOCH(CH_3)OC_2H_5$ and n is 0 (see the following structural formula (N))

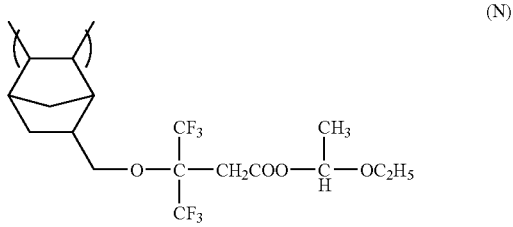

(N)

2 g of the polymer PG obtained in Example 12 was dissolved in 10 ml of THF, 1 g of ethyl vinyl ether and 0.032 g of pyridium p-toluenesulfonate were added to the solution, and the mixture was stirred at 0° C. for 24 hours. The reaction solution was poured into water, the deposited resin was separated by filtration. Further, the resin was dissolved in a small amount of acetone and reprecipitated in 100 ml of hexane to obtain 1.9 g of the intended polymer PH (yield: 90%).

Example 14

[Evaluation of Transparency of Polymers]

0.08 g of the polymer PA obtained in Example 6 was dissolved in 0.45 g of propylene glycol monomethyl ether acetate, and then the solution was filtered through a filter. Next, a calcium fluoride substrate was spin-coated with the filtrate, and baked on a hot plate at 110° C. for 120 seconds to form a thin film with a thickness of 0.1 μm. Transmittance at 157 nm as a center wavelength of $F_2$ excimer laser light of the thin film was measured using a vacuum ultraviolet spectrophotometer (VUV-201 manufactured by JASCO Corp.). The same measurement was carried out for the polymers obtained in Example 7, Example 8, Example 9, Example 10 and Example 13. For comparison, transmittance of poly(p-hydroxystyrene) as a resin for a KrF resist was measured. The results of measuring the transmittance of these polymers are shown in Table 1. FIG. 1 shows a transmittancy curve of a thin film of the polymer PA obtained in Example 6 (thickness: 0.1 μm).

TABLE 1

| Polymer | Light Transmittancy (%/0.1 μm) |
| --- | --- |
| Polymer PA | 65 |
| Polymer PB | 64 |
| Polymer PC | 63 |
| Polymer PD | 54 |
| Polymer PE | 52 |
| Polymer PH | 54 |
| Poly(p-hydroxystyrene) | 20 |

The results confirmed that the polymer of the present invention is highly transparent to light at 157 nm.

Example 15

[Exposure Test for Resist Using Polymer of Present Invention]

(a) 1.5 g of the polymer PB obtained in Example 7 and (b) 0.06 g of a photoacid generator (triphenylsulfonium nonaflate) were dissolved in (c) 10 g of propylene glycol monomethyl ether acetate, and the solution was filtered through a 0.2 μm Teflon™ filter to prepare a resist solution. A 4-inch silicon substrate was spin-coated with the resist solution, and baked on a hot plate at 110° C. for two minutes to form a thin film with a thickness of 0.1 μm. Next, the thin film was exposed to light using an $F_2$ excimer laser with an exposure area of 5 mm×5 mm. Immediately after that, the substrate was baked on a hot plate at 130° C. for 60 seconds, immersed in a 2.38% aqueous solution of TMAH (($CH_3$)$_4$NOH) at a solution temperature of 23° C. for 60 seconds to develop the resist, and subsequently rinsed with pure water for 60 seconds. The relation between the exposure dose and the thickness of the remaining resist was examined to find that the resist had a thickness of 0 and exhibited behavior as a positive resist at an exposure dose of 15 mJ/cm².

The exposure dose for providing a resist thickness of 0 was measured also for the polymer PD obtained in Example 9, the polymer PE obtained in Example 10 and the polymer PH obtained in Example 13. The exposure dose for providing a resist thickness of 0 was 17 mJ/cm² for the polymer PD, 23 mJ/cm² for the polymer PE and 14 mJ/cm² for the polymer PH. Any of these polymers exhibited behavior as a positive resist.

Example 16

[Patterning Test for Resist Using Resin of Present Invention]

(a) 1.5 g of the polymer PB and (b) 0.06 g of a photoacid generator (triphenylsulfonium nonaflate) were dissolved in (c) 9 g of propylene glycol monomethyl ether acetate, and the solution was filtered through a 0.2 μm Teflon™ filter to prepare a resist solution. An 8-inch silicon substrate with a 0.1 μm-thick organic antireflection film applied thereto was spin-coated with the resist solution, and baked on a hot plate at 130° C. for one minute to form a thin film with a thickness of 0.3 μm. The thin film was pattern-exposed using ArF lithographic equipment (manufactured by Nikon Corp., NA=0.6). Immediately after that, the substrate was baked on a hot plate at 135° C. for 60 seconds, immersed in a 2.38% aqueous solution of TMAH at a solution temperature of 23° C. for 60 seconds to develop the resist, and subsequently rinsed with pure water for 60 seconds. As a result, only the exposed part of the resist film was dissolved in the developer and removed, and a positive pattern was obtained.

The same measurement was carried out for the polymer PD obtained in Example 9, the polymer PE obtained in Example 10 and the polymer PH obtained in Example 13. Table 2 shows the results of measuring the resolution and the sensitivity obtained from observation with an SEM (scanning electron microscope).

TABLE 2

| Polymer for resist | Resolution (μmL/S) | Sensitivity (mJ/cm$^2$) |
|---|---|---|
| Polymer PB | 0.17 | 23 |
| Polymer PD | 0.18 | 20 |
| Polymer PE | 0.17 | 26 |
| Polymer PH | 0.16 | 18 |

As is clear from the above results, the resist using the polymer of the present invention has excellent resolution characteristics.

(Evaluation of Adhesion to Substrate)

As a result of observing the substrates patterned above with an SEM (scanning electron microscope), it was confirmed that no pattern peeling or the like was found in any substrate, and the resist has sufficient adhesion to a substrate.

Example 17

[Evaluation of Etching Resistance]

2 g of the polymer PA was dissolved in 10 g of propylene glycol monomethyl ether acetate, and the solution was filtered through a filter. Next, a 3-inch silicon substrate was spin-coated with the filtrate, and baked on a hot plate at 90° C. for 60 seconds to form a thin film with a thickness of 0.7 μm. The rate of etching the resulting film with a $CF_4$ gas was measured using reactive ion etching (RIE) equipment (manufactured by Anelva Corp., DEM451) (etching conditions: power; 100 W, pressure; 5 Pa, gas flow rate; 30 ml/sec).

The etching rate was measured also for the polymer PB obtained in Example 7, the polymer PC obtained in Example 8, the polymer PD obtained in Example 9, the polymer PE obtained in Example 10 and the polymer PH obtained in Example 13. For comparison, the etching rate was measured also for poly(p-hydroxystyrene) used as a base resin of a KrF resist and poly(methyl methacrylate) as a resin not having a bridged cyclic hydrocarbon group in the molecular structure.

The results of measuring these polymers are shown in Table 3, with the rate of etching poly(p-hydroxystyrene) normalized as 1.

TABLE 3

| Polymer | Etching rate (relative ratio) |
|---|---|
| Polymer PA | 1.2 |
| Polymer PB | 1.2 |
| Polymer PC | 1.15 |
| Polymer PD | 1.2 |
| Polymer PE | 1.3 |
| Polymer PH | 1.2 |
| Poly(p-hydroxystyrene) | 1 |
| Poly(methyl methacrylate) | 1.65 |

The above results show that the polymer used in the present invention is etched by a $CF_4$ gas at a low rate, and thus has excellent dry etching resistance.

INDUSTRIAL APPLICABILITY

As is clear from the above description, the polymer using the compound of the present invention as a monomer has excellent transparency, adhesion to a substrate, and dry etching resistance as a chemically amplified resist for an $F_2$ excimer laser. The polymer of the present invention allows formation of a micropattern required for production of a semiconductor element by use thereof, and is thus advantageously used.

The invention claimed is:

1. An alicyclic unsaturated compound represented by the following general formula (1):

$$\text{(1)}$$

wherein $R^1$ and $R^2$ independently represent a hydrogen atom, a fluorine atom, a linear, branched or cyclic alkyl group having 1 to 6 carbon atoms or a fluorinated alkyl group, and at least one of $R^1$ and $R^2$ is a fluorine atom or a fluorinated alkyl group, $R^3$ represents a hydrogen atom, a linear, branched or cyclic alkyl group having 1 to 6 carbon atoms, a fluorinated alkyl group, a carboxymethyl group or a group that is decomposed by the action of an acid, $R^4$ represents a hydrogen atom, a linear, branched or cyclic alkyl group having 1 to 6 carbon atoms, a fluorinated alkyl group, an acetyl group, a chloroacetyl group or a group that is decomposed by the action of an acid, $R^5$ represents a hydrogen atom, a linear, branched or cyclic alkyl group having 1 to 6 carbon atoms or a fluorinated alkyl group, $A^1$ and $A^2$ independently represent a hydrogen atom or a methyl group, $X^1$ and $X^2$ independently represent $-CH_2-$, $-CH_2CH_2-$ or $-O-$, Y is a hydrogen atom, a methyl group or a fluorine atom, m is 0 or 1, n1 and n2 are independently an integer of 0 to 2, and at least one of n1 and n2 is non-zero.

2. The alicyclic unsaturated compound according to claim 1, wherein $X^1$ and $X^2$ independently represent $-CH_2CH_2-$ or $-O-$.

3. The alicyclic unsaturated compound according to claim 1, wherein at least one of $A^1$ and $A^2$ is a methyl group.

4. The alicyclic unsaturated compound according to claim 1, wherein $R^5$ comprises a fluorinated alkyl group.

5. A polymer obtained by polymerizing a polymer precursor containing at least one compound of the following general formula (1):

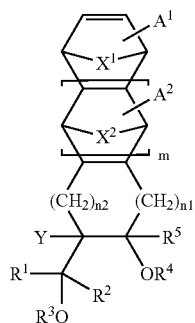

(1)

wherein
- $R^1$ and $R^2$ independently represent a hydrogen atom, a fluorine atom, a linear, branched or cyclic alkyl group having 1 to 6 carbon atoms or a fluorinated alkyl group, and at least one of $R^1$ and $R^2$ is a fluorine atom or a fluorinated alkyl group,
- $R^3$ represents a hydrogen atom, a linear, branched or cyclic alkyl group having 1 to 6 carbon atoms, a fluorinated alkyl group, a carboxymethyl group or a group that is decomposed by the action of an acid,
- $R^4$ represents a hydrogen atom, a linear, branched or cyclic alkyl group having 1 to 6 carbon atoms, a fluorinated alkyl group, an acetyl group, a chloroacetyl group or a group that is decomposed by the action of an acid,
- $R^5$ represents a hydrogen atom, a linear, branched or cyclic alkyl group having 1 to 6 carbon atoms or a fluorinated alkyl group,
- $A^1$ and $A^2$ independently represent a hydrogen atom or a methyl group,
- $X^1$ and $X^2$ independently represent —$CH_2$—, —$CH_2CH_2$— or —O—,
- Y represents a hydrogen atom, a methyl group or a fluorine atom,
- m is 0 or 1,
- n1 and n2 are independently an integer of 0 to 2, and
- at least one of n1 and n2 is non-zero.

6. The polymer according to claim 5, comprising one or more repeating structural units represented by the following general formula (2):

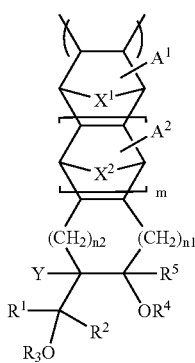

(2)

wherein
- $R^1$ and $R^2$ independently represent a hydrogen atom, a fluorine atom, a linear, branched or cyclic alkyl group having 1 to 6 carbon atoms or a fluorinated alkyl group, and at least one of $R^1$ and $R^2$ is a fluorine atom of a fluorinated alkyl group,
- $R^3$ represents a hydrogen atom, a linear, branched or cyclic alkyl group having 1 to 6 carbon atoms, a fluorinated alkyl group, a carboxymethyl group or a group that is decomposed by the action of an acid,
- $R^4$ represents a hydrogen atom, a linear, branched or cyclic alkyl group having 1 to 6 carbon atoms, a fluorinated alkyl group, an acetyl group, a chloroacetyl group or a group that is decomposed by the action of an acid, $R^5$ represents a hydrogen atom, a linear, branched or cyclic alkyl group having 1 to 6 carbon atoms or a fluorinated alkyl group,
- $A^1$ $A^2$ independently represent a hydrogen atom or a methyl group,
- $X^1$ and $X^2$ independently represent —$CH_2$—, —$CH_2CH_2$— or —O—,
- Y represents a hydrogen atom, a methyl group or a fluorine atom,
- m is 0 or 1, and n1 and n2 are independently art integer of 0 to 2.

7. The polymer according to claim 6, further comprising at least one of structural units represented by the following general formulas (3) to (9):

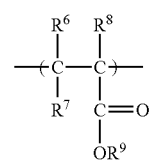

(3)

wherein
- $R^6$ and $R^7$ independently represent a hydrogen atom or a fluorine atom,
- $R^8$ is a hydrogen atom, a fluorine atom, a methyl group or a trifluoromethyl group, and
- $R^9$ represents a hydrogen atom, a linear, branched or cyclic alkyl group having 1 to 20 carbon atoms, a fluorinated alkyl group, a group that is decomposed by the action of an acid, an alicyclic hydrocarbon group having 7 to 13 carbon atoms which has a group that is decomposed by the action of an acid, or a 2,6-norbornanecarbolactone-5-yl group;

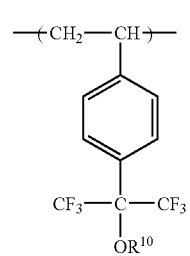

(4)

wherein
- $R^{10}$ represents a hydrogen atom or a group that is decomposed by the action of an acid;

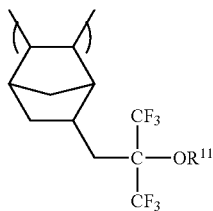

wherein
$R^{11}$ represents a hydrogen atom or a group that is decomposed by the action of an acid;

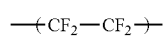

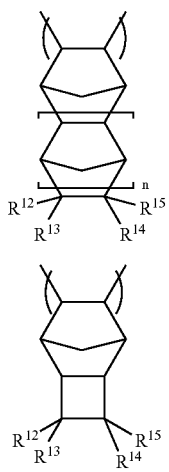

wherein
$R^{12}$, $R^{13}$, $R^{14}$ and $R^{15}$ independently represent a hydrogen atom, a fluorine atom, a methyl group, a trifluoromethyl group, a hydroxy group, a hydroxyalkyl group, a carboxy group (—COOH), —CH$_2$OH(CF$_3$)$_2$CH$_2$COOZ$^5$ (wherein $Z^5$ is a hydrogen atom or a group that is decomposed by the action of an acid) or an acid-dissociable organic group having 20 or less carbon atoms which is decomposed by the action of an acid to produce a carboxy group, and n is 0 or 1; and

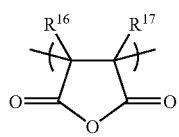

wherein
$R^{16}$ and $R^{17}$ independently represent a hydrogen atom, a fluorine atom or a trifluoromethyl group.

8. A chemically amplified resist composition comprising at least the polymer according to claim 7 and a photoacid generator which generates an acid upon exposure, wherein the photoacid generator is 0.2 to 30% by weight based on the polymer and the photoacid generator in total.

9. The polymer according to claim 6, wherein the structural unit represented by the general formula (2) is contained in the polymer at 5 to 100 mol %.

10. A chemically amplified resist composition comprising at least the polymer according to claim 9 and a photoacid generator which generates en acid upon exposure, wherein the photoacid generator is 0.2 to 30% by weight based on the polymer and the photoacid generator in total.

11. The polymer according to claim 6, which has a weight average molecular weight of 2,000 to 200,000.

12. A chemically amplified resist composition comprising at least the polymer according to claim 11 and a photoacid generator which generates an acid upon exposure, wherein the photoacid generator is 0.2 to 30% by weight based on the polymer and the photoacid generator in total.

13. A chemically amplified resist composition comprising at least the polymer according to claim 6 and a photoacid generator which generates an acid upon exposure, wherein the photoacid generator is 0.2 to 30% by weight based on the polymer and the photoacid generator in total.

14. A chemically amplified resist composition comprising at least the polymer according to claim 5 and a photoacid generator which generates an acid upon exposure, wherein the photoacid generator is 0.2 to 30% by weight based on the polymer and the photoacid generator in total.

15. A method for forming a pattern, comprising at least a step of coating a substrate to be processed with the chemically amplified resist composition according to claim 14, a step of exposing the resist to light at a wavelength of 130 to 190 nm, and a step of developing the resist.

16. The method for forming a pattern according to claim 15, wherein the exposure light is F2 excimer laser light.

17. The polymer according to claim 5, wherein $X^1$ and $X^2$ independently represent —CH$_2$CH$_2$— or —O—.

18. The polymer according to claim 5, wherein at least one of $A^1$ and $A^2$ is a methyl group.

19. The polymer according to claim 5, wherein $R^5$ comprises a fluorinated alkyl group.

20. An alicyclic unsaturated compound represented by the following general formula (1):

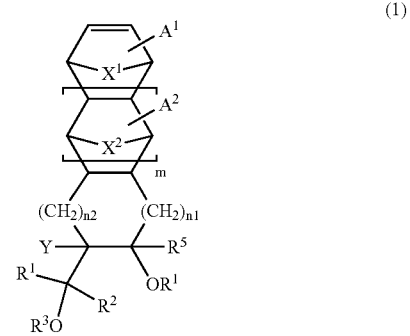

wherein
$R^1$ and $R^2$ independently represent a hydrogen atom, a fluorine atom, a linear, branched or cyclic alkyl group having 1 to 6 carbon atoms or a fluorinated alkyl group, and at least one of $R^1$ and $R^2$ is a fluorine atom or a fluorinated alkyl group, $R^3$ represents a hydrogen atom, a linear, branched or cyclic alkyl group having 1 to 6 carbon atoms, a fluorinated alkyl group, a carboxymethyl group or a group that is decomposed by the action of an acid, $R^4$ represents a fluorinated alkyl group, an acetyl group, or a chloroacetyl group, $R^5$ represents a hydrogen atom, a linear, branched or cyclic alkyl group having 1 to 6 carbon atoms or a fluorinated alkyl group, $A^1$ and $A^2$ independently represent a hydrogen atom or a methyl group, $X^1$ and $X^2$ independently represent $-CH_2-$, $-CH_2CH_2-$ or $-O-$, Y is a hydrogen atom, a methyl group or a fluorine atom, m is 0 or 1, n1 and n2 are independently an integer of 0 to 2.

* * * * *